(12) United States Patent
Tsai et al.

(10) Patent No.: US 9,080,939 B2
(45) Date of Patent: Jul. 14, 2015

(54) METHOD OF MEASURING GLYCOSYLATED PROTEIN PROPORTION BY AC IMPEDANCE METHOD

(71) Applicant: National Central University, Zhongli, Taoyuan County (TW)

(72) Inventors: Jang-Zern Tsai, Zhongli (TW); Ching-Jung Chen, Zhongli (TW); Yung-Nien Wei, Zhongli (TW)

(73) Assignee: NATIONAL CENTRAL UNIVERSITY, Zhongli (TW)

( * ) Notice: Subject to any disclaimer, the term of this patent is extended or adjusted under 35 U.S.C. 154(b) by 238 days.

(21) Appl. No.: 13/786,656

(22) Filed: Mar. 6, 2013

(65) Prior Publication Data

US 2013/0233727 A1     Sep. 12, 2013

(30) Foreign Application Priority Data

Mar. 6, 2012   (TW) ............................... 10117510 A (51) Int. Cl.
  *G01N 27/02*     (2006.01)
  *G01N 33/49*     (2006.01)

(52) U.S. Cl.
  CPC .............. *G01N 27/02* (2013.01); *G01N 27/026* (2013.01); *G01N 33/49* (2013.01)

(58) Field of Classification Search
  CPC ............................ G01N 27/02; G01N 33/543
  USPC .................................. 205/780.5, 787; 435/7.8
  See application file for complete search history.

(56) References Cited

U.S. PATENT DOCUMENTS

| 6,846,639 B2 * | 1/2005 | Miles et al. ..................... 435/7.1 |
| 2011/0123399 A1 * | 5/2011 | Nam et al. ..................... 422/69 |

FOREIGN PATENT DOCUMENTS

WO     WO 2012/009322     *   1/2012

OTHER PUBLICATIONS

Iles et al. (Biomedical Science, 2012, 2:4).*
Zhang et al. (Analyst, 2008, 485-492).*
Park et al. (Pure Appl. Chem., vol. 78, No. 5, pp. 1069-1080, 2006).*
Sheikholeslam et al. (Biosensors for Health, Environment and Biosecurity, 2011).*

* cited by examiner

*Primary Examiner* — Jennifer Dieterle
(74) *Attorney, Agent, or Firm* — Muncy, Geissler, Olds & Lowe, P.C.

(57) ABSTRACT

A method of measuring a glycosylated protein proportion by an AC impedance method includes passing an AC voltage or AC to two inspecting electrodes; covering a solution containing glycosylated protein completely onto the inspecting electrodes; measuring an impedance value between the electrodes and calculating the difference between the impedance value and an impedance value of a solution without glycosylated protein by an AC impedance inspection device; comparing the impedance difference with AC impedance difference/glycosylated protein concentration to obtain the proportion of the glycosylated protein in the solution containing glycosylated protein. The solution without glycosylated protein includes a salt solution and a non-glycosylated protein; the proportion of glycosylated protein in the solution containing glycosylated protein refers to the proportion of glycosylated protein in the total quantity of protein in the salt solution; and the proportion of glycosylated hemoglobin of the total quantity of hemoglobin in the salt solution.

13 Claims, 6 Drawing Sheets

METHOD OF MEASURING GLYCOSYLATED PROTEIN PROPORTION BY AC IMPEDANCE METHOD

FIELD OF THE INVENTION

The present invention relates to a method of measuring a glycosylated protein proportion by an AC impedance method.

BACKGROUND OF THE INVENTION

In general, blood glucose level is used as an index for controlling diabetes, and the blood glucose level approaching a normal value indicates a good control of the blood glucose. Related blood glucose measurement techniques such as those disclosed in R.O.C. Pat. No. M384315 entitled "Non-Invasive Optical Blood Glucose Detector", R.O.C. Pat. No. 1295566 entitled "Blood Glucose Detection Instrument with Blood Collection Gun, or U.S. Pat. Publication No. 2009/0292186 entitled "Method and System for Non-Invasive Optical Blood Glucose Detection Utilizing Spectral Data Analysis" measure the blood glucose level in blood directly.

However, the blood glucose varies with time and diet significantly, and the blood glucose measurement just indicates the blood glucose value at the time of the measurement only, so that such measurement of the blood glucose level cannot be used solely as an the absolute diabetic control index.

In the red blood cell of a regular person, the percentage of hemoglobin (Hb) is over 95%. If a human body loses control of insulin, a large quantity of glucose will be released from the blood, and the glucose in the blood will be combined slowly with the Hb to form glycosylated hemoglobin ($HbA_1C$). Since the process of forming $HbA_1C$ is slow, it takes time to form and accumulate $HbA_1C$, so that the level of $HbA_1C$ relates to the daily average blood glucose concentration and does not change immediately with the blood glucose concentration before or after meals, and the blood glucose level measured after meals will not have a big difference. Based on the extent of combining glucose and Hb, World Health Organization (WHO) points out that if the glycosylated hemoglobin of a person occupies more than 6.5% of the total quantity of hemoglobin, the person is considered as a diabetic patient.

In recent years, the measurement of $HbA_1C$ content is used extensively for monitoring an average blood glucose level of the diabetic patient. In addition, the red blood cell has a life of approximately 3 months, so that the blood glucose control condition obtained by taking the $HbA_1C$ content approximately three months ago can be used for monitoring and controlling the blood glucose condition and serving as a basis for adjusting dosage. According to the estimation made by the International Diabetes Federation, the world's population of diabetic patients is approximately equal to two hundred millions and expected to be over three hundred millions by 2025. Obviously, the detection of $HbA_1C$ is a huge business opportunity that is worth for R&D investments, and a quick and convenient $HbA_1C$ detection technique can help diabetic patients to control their blood glucose level and reduce the occurrence of complications.

As to the related $HbA_1C$ detection techniques, "Method and apparatus for rapid measurement of $HbA_1C$" as disclosed in U.S. Pat. No. 6,582,964 adopts an optical inspection method; "Method of measuring $HbA_1C$" as disclosed in U.S. Pat. Publication No. US2010/0178659 adopts an enzyme detection method; and other methods adopting an electrochemical measurement method, wherein there are two types of electrochemical measurement methods, respectively: DC electrochemical measurement method and AC electrochemical measurement method. As to biosensors, the AC measurement such as the "Systems and methods for replacing signal artifacts in a glucose sensor data stream" disclosed in U.S. Pat. No. 7,998,017 is usually adopted. The AC measurement method mainly uses a cyclic voltammetry, but the electron transfer of the inspecting electrodes will be reduced after the conductivity at the surface of the inspecting electrodes is decreased and the surface is modified. Now, the cyclic voltammetry cannot measure the inspecting electrodes and an object to be tested properly.

The AC impedance measurement method can overcome the aforementioned shortcoming, and thus an AC impedance glycosylated protein measurement such as the "Device for measuring proteins using biosensor" as disclosed in U.S. Pat. No. 2011/0123399 was introduced.

Further, AC stimulation such as the "Method for treatment of diabetes by electrostimulation" as disclosed in U.S. Pat. No. US 2009/0254133 is used as a technical measure for treating diabetes, and this method discloses an AC stimulation with a frequency between 0.00065 Hz and 0.00085 Hz and an ampere between 20 mA and 1 atto (10 A~18 A) for treating and controlling insulin to stabilize the blood glucose of insulin dependent diabetic patients.

SUMMARY OF THE INVENTION

In view of the advantages of the AC impedance measurement, the present invention can use an AC impedance electrochemical biosensor chip to distinguish different changes between biomolecules according to the change of frequency, voltage, current, impedance or phase obtained from the basic electrical property of the biomolecules, so that the impedance electrochemical biosensor chip can be used together with the AC impedance method to distinguish the difference between glycosylated protein and non-glycosylated protein. For example, glycosylated hemoglobin ($HbA_1C$) and hemoglobin (Hb) can be used to determine the glycosylated hemoglobin in the total quantity of hemoglobin proportion.

The glycosylated protein and non-glycosylated protein are detected and measured in a salt solution compatible to human tissue cells to avoid modifications after the glycosylated protein and non-glycosylated protein are removed from a human body. Further, the effect of charged ions produced by the dissociation of the salt solution on the increase of signal gains and interference in the detection of the glycosylated protein and non-glycosylated protein is taken into consideration, so that the salt solution is diluted.

To achieve the aforementioned objective, the present invention provides a method of measuring a glycosylated protein proportion by an AC impedance method, comprising the steps of: passing an alternating current (AC) voltage or an alternating current (AC) to a pair of inspecting, electrodes, and covering the inspecting electrodes completely by a solution containing a glycosylated protein, and obtaining an impedance value between the electrodes through an AC impedance inspection device; calculating the impedance difference between the impedance value and an impedance value of a solution without the glycosylated protein; and comparing the impedance difference with a relation of AC impedance difference/glycosylated protein concentration to obtain the proportion of the glycosylated protein in a solution containing the glycosylated protein.

Wherein, the relation of AC impedance difference/glycosylated protein concentration is created by obtaining impedance values of a solution A without glycosylated protein and a solution B without glycosylated protein by the AC impedance inspection device after glycosylated proteins in different concentrations are dissolved therein, and obtaining an impedance difference between the solutions A and B and a curve of the impedance difference after glycosylated proteins of different concentrations are dissolved in the solution without glycosylated protein, and using the curve to obtain the relation of AC impedance difference/glycosylated protein concentration required for the inspection. In addition, the solution without glycosylated protein includes a salt solution and a non-glycosylated protein.

In addition, the glycosylated protein is glycosylated hemoglobin, and the total quantity of the glycosylated hemoglobin and the non-glycosylated hemoglobin are defined as the total quantity of hemoglobin, and the proportion of the glycosylated hemoglobin in a solution containing glycosylated hemoglobin refers the proportion of the glycosylated hemoglobin in the total quantity of hemoglobin contained in the salt solution. The proportion of the glycosylated hemoglobin contained in the total quantity of hemoglobin falls within a range from 0% to 10%. In addition, the relation of AC impedance difference/glycosylated protein concentration is a relation of AC impedance difference/glycosylated hemoglobin concentration.

The present invention has the following effects. The relation of AC impedance difference/glycosylated protein concentration is established in advance and used during the inspection of the glycosylated hemoglobin ($HbA_1C$) and the non-glycosylated hemoglobin (Hb) in order to obtain the proportion of the glycosylated hemoglobin ($HbA_1C$) in the total quantity of hemoglobin easily, and this is a quick simple, and accurate method for determining whether a person is a diabetic patient, or an inspection method for observing a diabetic patient's blood glucose control condition.

DESCRIPTION OF THE PREFERRED EMBODIMENTS

The present invention will become clearer in light of the following detailed description of an illustrative embodiment of this invention described in connection with the drawings. It is intended that the embodiments and drawings disclosed herein are to be considered illustrative rather than restrictive.

Hemoglobin is a protein, so that glycosylated hemoglobin ($HbA_1C$) is used as an example of the glycosylated protein and non-glycosylated protein is used as non-glycosylated hemoglobin (Hb) in this preferred embodiment, and the total quantity of the glycosylated hemoglobin ($HbA_1C$) and the non-glycosylated hemoglobin (Hb) is defined as the total quantity of hemoglobin.

Firstly, it is noteworthy that when the AC impedance of Hb and $HbA_1C$ are measured, the samples of Hb and $HbA_1C$ must be dissolved in a salt solution to avoid modification after the Hb and $HbA_1C$ are removed from human body. To take the too-high concentration of salt ions creating a substantial interference during the measurement into consideration, the present invention dilutes the salt ions with deionized water, and the salt solution is equivalent to physiological saline water with a concentration in terms of percentage by volume ranging from 0.01% to 90%, and the salt solution is preferably diluted to the percentage by volume from 0.01% to 1%, and the salt solution such as physiological saline water or phosphate buffer solution (PBS) is compatible with human tissue cells, wherein the PBS can be prepared by dissolving a tablet of PBS into 100 ml of deionized water, and the tablet of PBS contains 10 mMol of phosphate, 137 mMol of sodium chloride and 2.7 mMol of potassium chloride and then the PBS solution is diluted by deionized water.

Figure 1:
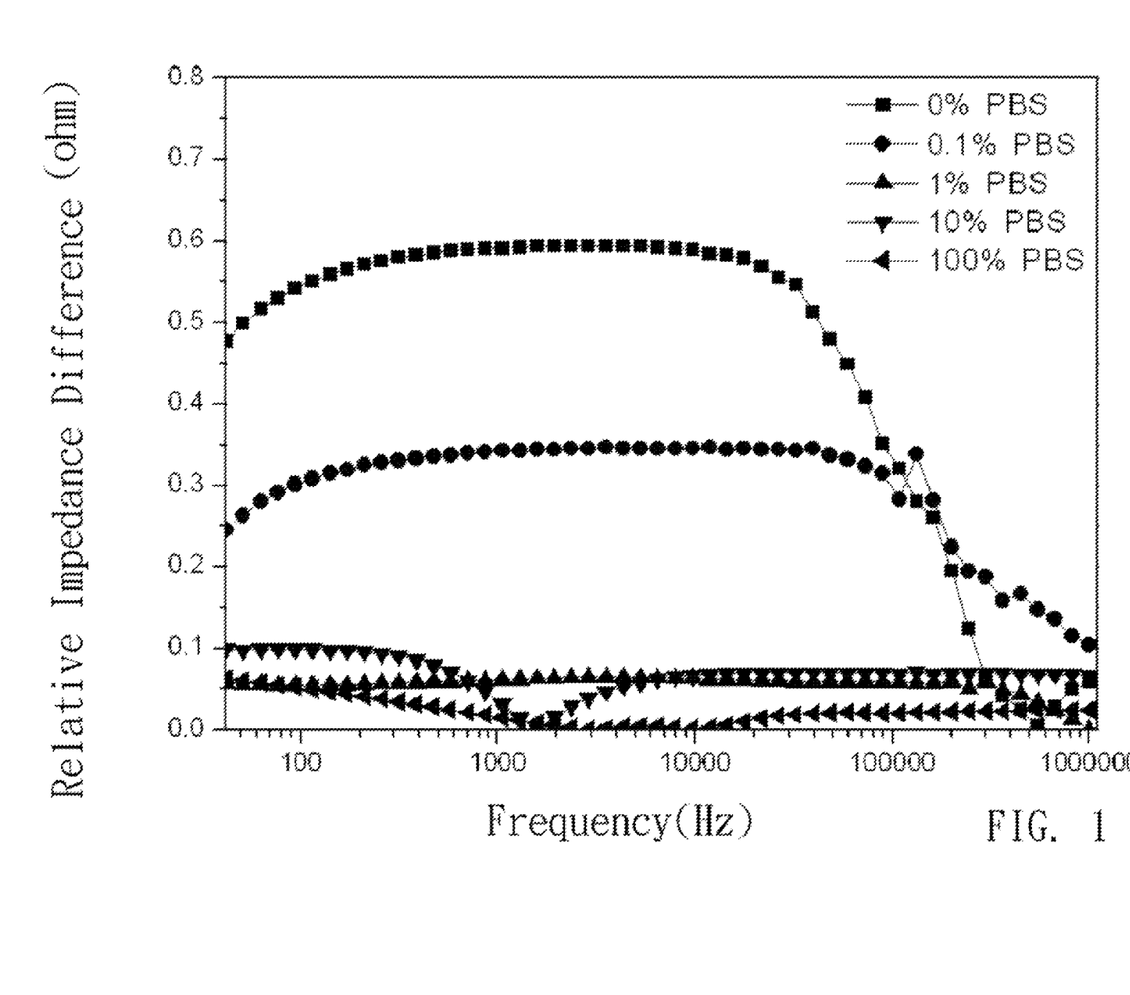
FIG. 1 shows an impedance spectroscopy in form of a frequency versus relative impedance difference dZ graph of a non-glycosylated hemoglobin dissolved in different dilute salt solutions in accordance with a preferred embodiment of the present invention.

With reference to FIG. 1 for an impedance spectroscopy in form of a frequency versus relative impedance difference dZ graph of a non-glycosylated hemoglobin dissolved in different dilute salt solutions in accordance with a preferred embodiment of the present invention, inspecting electrodes are used for measuring AC impedance of salt solutions with different concentration of Hb dissolved therein under different frequencies, and an impedance spectroscopy of the relative impedance difference (dZ) is drawn to illustrate the salt solution used in the present, and the concept of the impedance difference (dZ) can be expressed by the following equation (i):

$$dZ = \left| \frac{Z_{Hb} - Z_{bg}}{Z_{bg}} \right| \qquad (i)$$

Where, dZ is the relative impedance difference, ZHb is the impedance value of a salt solution containing Hb, and Zbg is the impedance value of a pure salt solution. The parameters shown in the figure are set as follows: the inputted AC voltage is 20 mV, the frequency is from 42 Hz to 1 MHz, and the Hb concentration is 0.2 mg/ml.

In the impedance spectroscope as shown FIG. 1, the higher the salt concentration of the salt solution, the smaller is the relative impedance difference dZ. Therefore, the test sample of Hb should be dissolved in the salt solution. Since the too-high concentration of the salt ions will interfere the measurement of the AC impedance and result in insignificant relative impedance difference dZ, so that the salt solution is diluted to a concentration with a percentage by volume from 0.01% to 90% and preferably from 0.01% to 1%.

Figure 2:
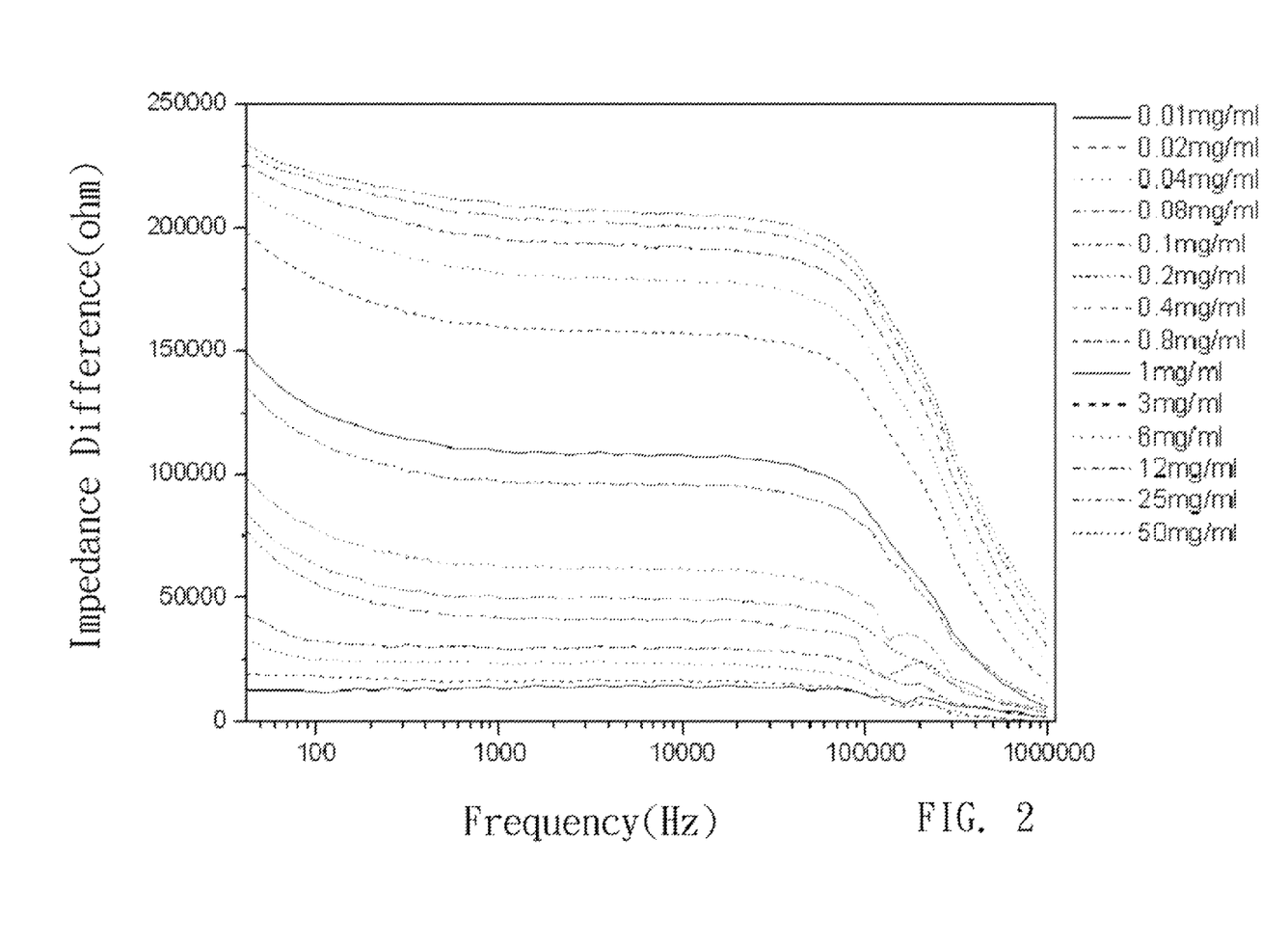
FIG. 2 shows an impedance spectroscopy in form of a frequency versus relative impedance difference DeltaZ graph of Hb in different concentrations in accordance with a preferred embodiment of the present invention.
Figure 3:
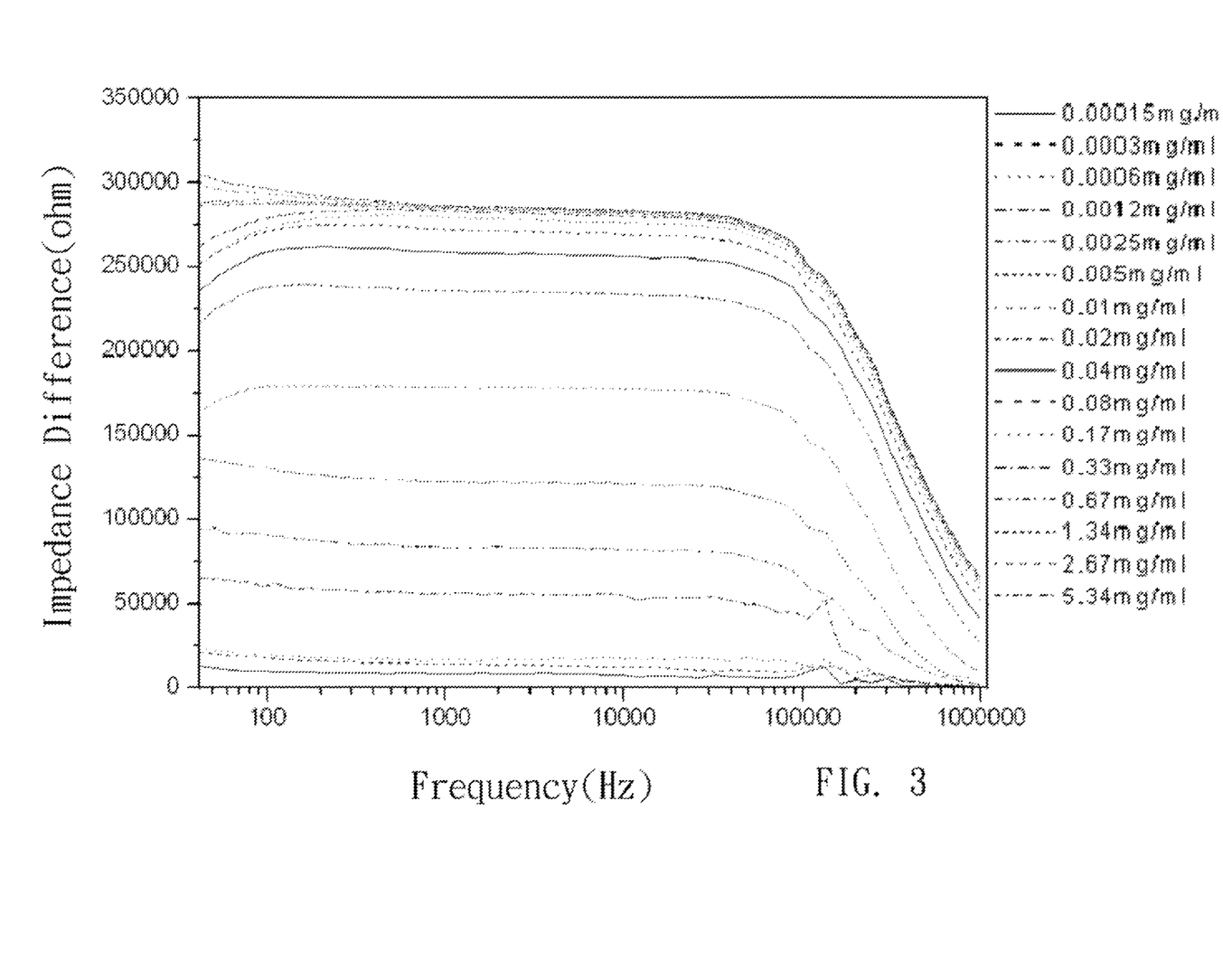
FIG. 3 shows an impedance spectroscopy in form of a frequency versus relative impedance difference DeltaZ graph of $HbA_1C$ in different concentrations in accordance with a preferred embodiment of the present invention.
Figure 4:
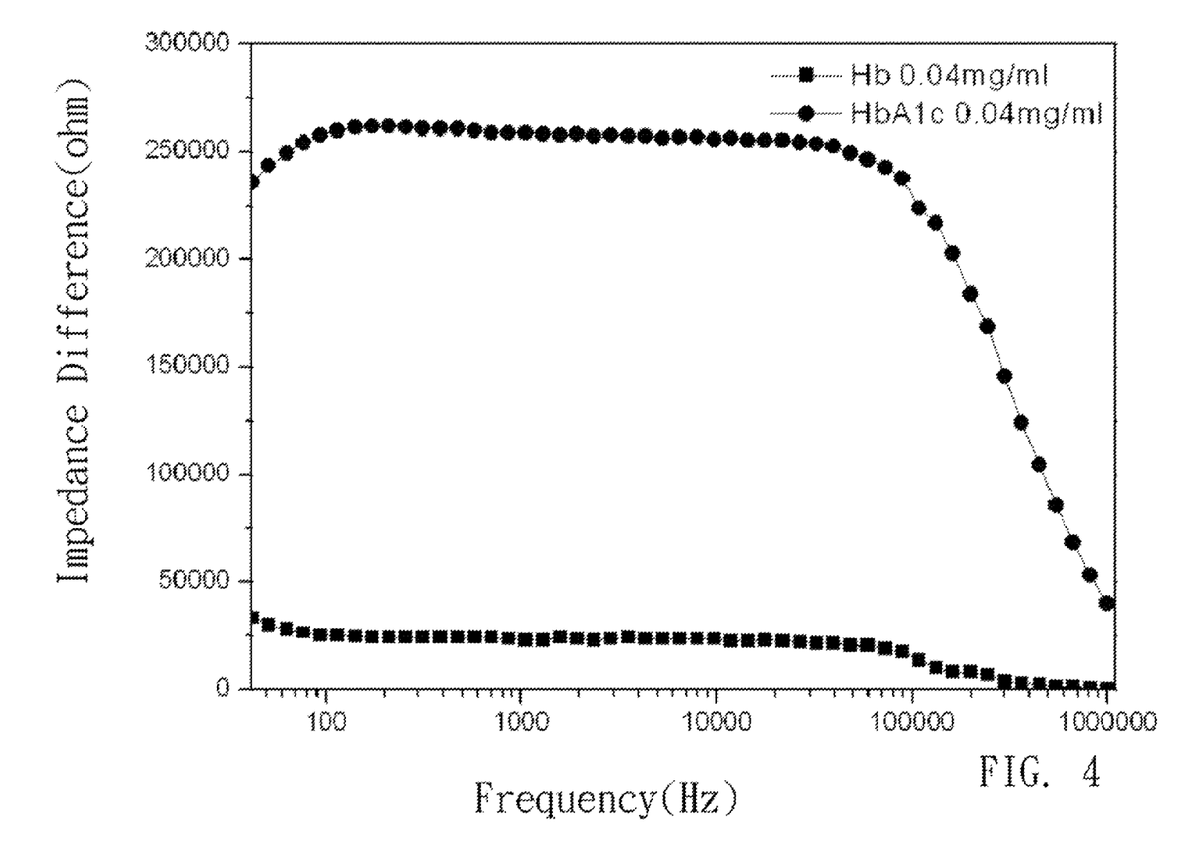
FIG. 4 shows an impedance spectroscopy in form of a frequency versus relative impedance difference DeltaZ graph of Hb and $HbA_1C$ of the same concentration in accordance with a preferred embodiment of the present invention.

In FIGS. 2 and 3, the curves of impedance difference between Hb and $HbA_1C$ of different concentrations at different frequencies are plotted, and the impedance spectroscopy with the same concentration of 0.04 mg/ml is used for comparison. The Hb and $HbA_1C$ of the same concentration have an impedance difference. At the frequency of 5.3 kHz, the impedance difference of Hb is approximately equal to 23.8 kΩ, the impedance difference of HbA₁C is approximately equal to 256.51 KΩ, and the two have a big difference, so that it is expected that the Hb and the HbA₁C with the same concentration of 0.04 mg/ml and different proportions dissolved in the salt solutions have an impedance difference falling between the two.

Figure 5:
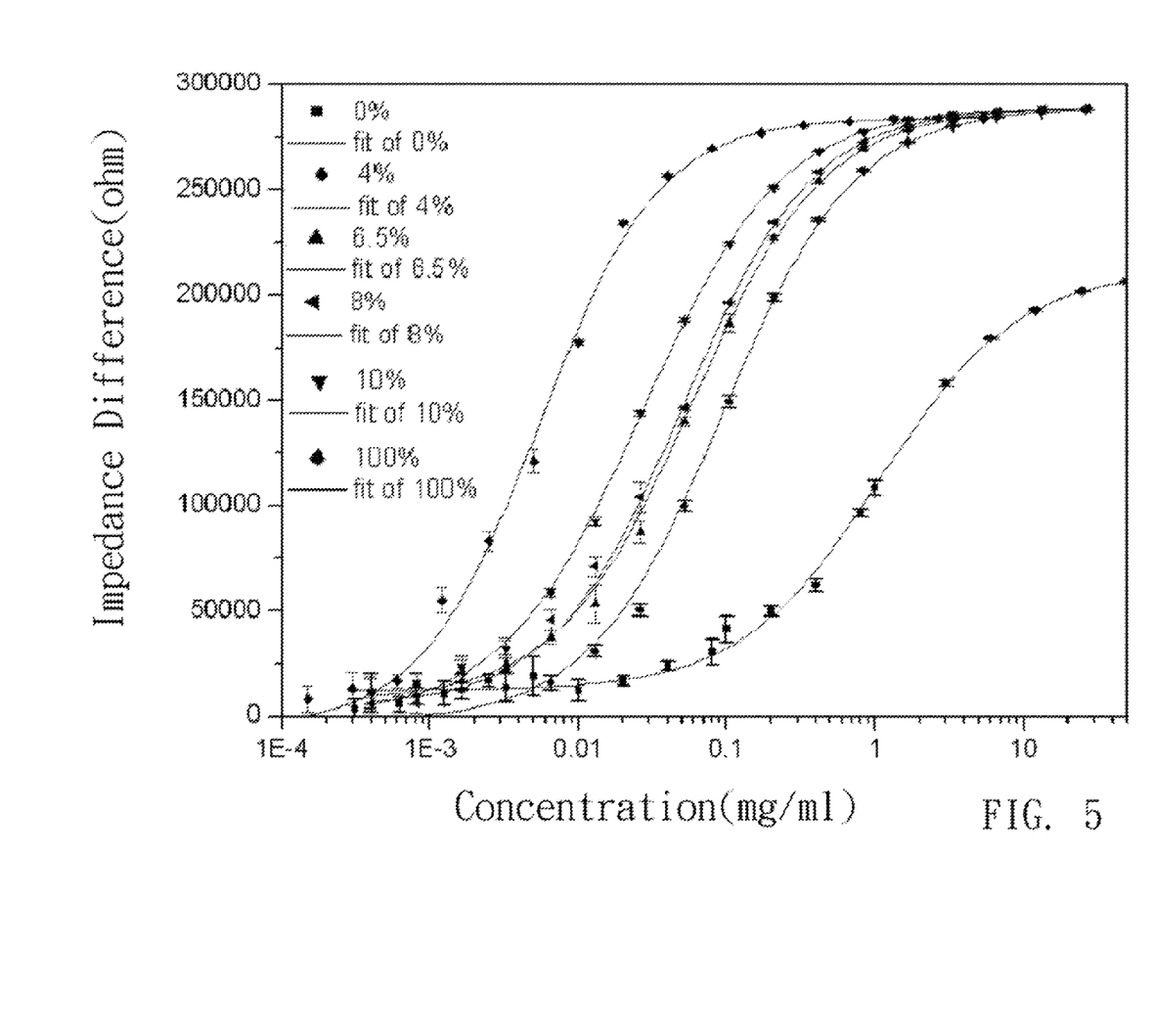
FIG. 5 shows an impedance spectroscopy in form of a concentration versus relative impedance difference DeltaZ graph of $HbA_1C$ with different proportions of the total quantity of hemoglobin at a constant frequency band in accordance with a preferred embodiment of the present invention.
Figure 6:
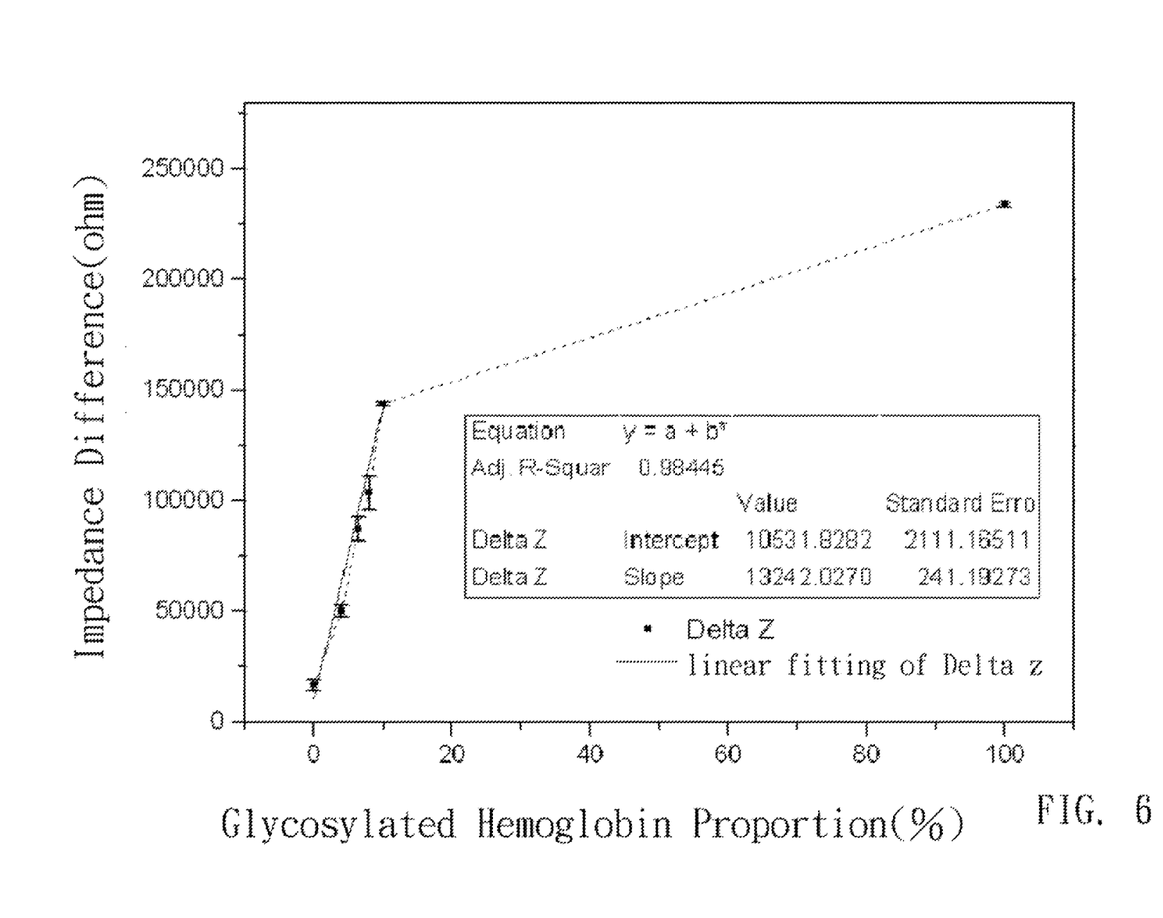
FIG. 6 shows an impedance spectroscopy in form of a concentration versus relative impedance difference graph of $HbA_1C$ with different proportions of the total quantity of hemoglobin as depicted in FIG. 5 at a constant concentration.

With reference to FIGS. 5 and 6 for the experiment results, the method of the present invention uses glycosylated hemoglobin and hemoglobin as examples for illustrating the invention.

Firstly, an AC voltage or AC is passed to a pair of inspecting electrodes for the inspection. Glycosylated hemoglobins of different concentrations are dissolved in a solution A without any glycosylated hemoglobin and a solution B without any glycosylated hemoglobin by an AC impedance inspection device to obtain the impedance values of the solutions A and B, wherein the solution without any glycosylated hemoglobin comprises a salt solution and a non-glycosylated hemoglobin, and after the impedance difference between the solutions A and B are obtained to plot the curve of the impedance difference between the solution without any glycosylated hemoglobin with glycosylated hemoglobins of different concentrations dissolved therein, and this curve is used to obtain a relation of AC impedance difference/glycosylated hemoglobin concentration required for the inspection. Further, a full-spectrum scan of the AC voltage or AC is performed, and the spectral region falls within a range from 1 Hz to 1 MHz, wherein the impedance value in the spectral region of this preferred embodiment at the constant frequency band of 5.3 KHz is used for comparing and analyzing the glycosylated hemoglobin proportion and the impedance difference.

It is noteworthy that glycosylated hemoglobins of different concentrations are dissolved in the solution without any glycosylated hemoglobin refers the glycosylated hemoglobin and the non-glycosylated hemoglobin of different proportions being dissolved in the salt solution proportion. In view of the recommendation made by WHO, a person with a HbA₁C exceeding 6.5% is considered as a diabetic patient, this preferred embodiment adopts a sample of the glycosylated hemoglobin having a proportion equal to 0% to 10% of the total quantity of hemoglobin, so that the total quantity of hemoglobin dissolved in the salt solution has a concentration controlled within a range greater than 0.001 mg/ml and smaller than 1 mg/ml. In FIG. 5, if the concentration of the total quantity of hemoglobin in the salt solution falls within a range from 0.001 mg/ml to 1 mg/ml, the slope is large, indicating a high sensitivity. A specific concentration from the curve as shown in FIG. 5 can be used for obtaining the curve as shown in FIG. 6.

In the process of detecting the proportion of the glycosylated hemoglobin proportion, an AC voltage or AC is passed to a pair of inspecting electrodes, and a solution containing glycosylated hemoglobin is covered completely onto the inspecting electrodes, and the AC impedance inspection device is provided for obtaining an impedance value between the electrodes and calculating the impedance difference between the pre-measured impedance value and an impedance of the solution without glycosylated hemoglobin, and the impedance difference is compared with a relatoin of the AC impedance difference/glycosylated hemoglobin concentration to obtain the proportion of glycosylated hemoglobin in the solution containing glycosylated hemoglobin. Since the solution without glycosylated hemoglobin includes a salt solution and a non-glycosylated hemoglobin, therefore the proportion of the glycosylated hemoglobin in the solution containing glycosylated hemoglobin refers to the proportion of the glycosylated hemoglobin in the total quantity of hemoglobin contained in the salt solution, so that we can know about the hemoglobin glycosylation condition of a patient and use it to determine diabetes or observe a diabetic patient's blood glucose control condition.

In summation of the description above, the present invention improves over the prior art, and is thus duly filed for patent application. While the invention has been described by means of specific embodiments, numerous modifications and variations could be made thereto by those skilled in the art without departing from the scope and spirit of the invention set forth in the claims.

What is claimed is:

1. A method of measuring a glycosylated protein proportion by and AC impedance method, comprising the steps of:
   passing an alternating current (AC) voltage or an alternating current (AC) to a pair of inspecting electrodes, and covering the inspecting electrodes completely by a solution containing a glycosylated protein, and obtaining an impedance value between the electrodes through an AC impedance inspection device;
   calculating the impedance difference between the impedance value and an impedance value of a salt and non-glycosylated protein solution without glycosylated protein;
   creating a plurality of reference curves defining the relationship between the concentration of glycosylated protein and the impedance difference for a range of AC frequencies;
   and comparing the impedance difference with a relation of AC impedance difference to glycosylated protein concentration to obtain the proportion of the glycosylated protein in the solution containing the glycosylated protein.

2. The method of measuring a glycosylated protein proportion by an AC impedance method according to claim 1, wherein the relation of AC impedance difference to glycosylated protein concentration is created by obtaining impedance values of a solution A without glycosylated protein and a solution B without glycosylated protein by the AC impedance inspection device after glycosylated proteins in different concentrations are dissolved therein, and obtaining an impedance difference between the solutions A and B and a curve of the impedance difference after glycosylated proteins of different concentrations are dissolved in the solution without glycosylated protein, and using the curve to obtain the relation of AC impedance difference to glycosylated protein concentration required for the inspection.

3. The method of measuring a glycosylated protein proportion by an AC impedance method according to claim 1, wherein the step passing an AC voltage or AC to the inspecting electrodes to obtain impedance values of a solution containing glycosylated protein and a solution without glycosylated protein further comprises the step of performing a full-spectrum scan of the AC voltage or AC, and the spectral region falls within a range from 1Hz to 1MHz.

4. The method of measuring a glycosylated protein proportion by an AC impedance method according to claim 3, wherein the step of passing an AC voltage or AC to the inspecting electrodes further comprises the step of obtaining an impedance value within the spectral region at a constant frequency band to compare and analyze the glycosylated protein proportion and the impedance difference.

5. The method of measuring a glycosylated protein proportion by an AC impedance method according to claim 1, wherein the salt solution is diluted by deionized water in advance, and the dilution percentage by volume is greater than 0.01% and smaller than 90%.

6. The method of measuring a glycosylated protein proportion by an AC impedance method according to claim 1, wherein the total quantity of the glycosylated protein and the non-glycosylated protein are defined as the total quantity of protein, and the proportion of the glycosylated protein in the solution containing glycosylated protein refers to the proportion of the glycosylated protein in the total quantity of protein contained in the salt solution.

7. The method of measuring a glycosylated protein proportion by an AC impedance method according to claim 6, wherein the glycosylated protein is glycosylated hemoglobin, and the non-glycosylated protein is non-glycosylated hemoglobin, and the total quantity of the glycosylated hemoglobin and the non-glycosylated hemoglobin is defined as a total quantity of hemoglobin, and the proportion of the glycosylated protein in the total quantity of protein refers to the proportion of the glycosylated hemoglobin in the total quantity of hemoglobin contained in the salt solution.

8. The method of measuring a glycosylated protein proportion by an AC impedance method according to claim 7, wherein the total quantity of hemoglobin contained in the salt solution has a concentration controlled to be greater than 0.001 mg/ml and smaller than 1mg/ml.

9. The method of measuring a glycosylated protein proportion by an AC impedance method according to claim 8, wherein the proportion of glycosylated hemoglobin in the total quantity of hemoglobin falls within a range from 0% to 10%.

10. The method of measuring a glycosylated protein proportion by an AC impedance method according to claim 1, wherein the glycosylated protein is glycosylated hemoglobin, and the solution containing glycosylated protein is a solution containing glycosylated hemoglobin, and the solution without glycosylated protein includes a salt solution and a non-glycosylated hemoglobin, and the total quantity of the glycosylated hemoglobin and the non-glycosylated hemoglobin is defined as the total quantity of hemoglobin, and the proportion of the glycosylated protein in a solution containing glycosylated protein refers to the proportion of the glycosylated hemoglobin in the total quantity of hemoglobin contained in the salt solution.

11. The method of measuring a glycosylated protein proportion by an AC impedance method according to claim 10, wherein the proportion of glycosylated hemoglobin in the total quantity of hemoglobin falls within a range from 0% to 10%.

12. The method of measuring a glycosylated protein proportion by an AC impedance method according to claim 10, wherein the relation of AC impedance difference to glycosylated protein concentration is a relation of AC impedance difference to glycosylated hemoglobin concentration created by obtaining impedance values of a solution A without glycosylated hemoglobin and a solution B without glycosylated hemoglobin by the AC impedance inspection device after glycosylated hemoglobins in different concentrations are dissolved therein, and obtaining an impedance difference between the solutions A and B and a curve of the impedance difference after glycosylated hemoglobins of different concentrations are dissolved in the solution without glycosylated hemoglobin, and using the curve to obtain the relation of AC impedance difference to glycosylated hemoglobin concentration required for the inspection.

13. The method of measuring a glycosylated protein proportion by an AC impedance method according to claim 10, wherein the step of passing an AC voltage or AC to the inspecting electrodes to obtain impedance values of a solution containing glycosylated hemoglobin and a solution without any glycosylated hemoglobin further comprises the step of performing a full spectrum scan of the AC voltage or AC, and the spectral region falls within a range from 1Hz to 1MHz.

* * * * *